United States Patent [19]
Anbar

[11] Patent Number: 5,999,843
[45] Date of Patent: Dec. 7, 1999

[54] DETECTION OF CANCEROUS LESIONS BY THEIR EFFECT ON THE SPATIAL HOMOGENEITY OF SKIN TEMPERATURE

[75] Inventor: Michael Anbar, Williamsville, N.Y.

[73] Assignee: OmniCorder Technologies, Inc., Williamsville, N.Y.

[21] Appl. No.: 09/063,129

[22] Filed: Apr. 20, 1998

Related U.S. Application Data

[63] Continuation-in-part of application No. 08/368,161, Jan. 3, 1995, Pat. No. 5,810,010.

[51] Int. Cl.$^6$ .................................................. A61B 6/00
[52] U.S. Cl. ......................... 600/474; 600/549; 600/504
[58] Field of Search .................................. 600/473, 474, 600/475, 549, 555, 504

[56] References Cited

U.S. PATENT DOCUMENTS

| | | | |
|---|---|---|---|
| 4,809,701 | 3/1989 | Le Bihan et al. | 600/407 |
| 5,205,293 | 4/1993 | Ito et al. | 128/691 |
| 5,207,222 | 5/1993 | Koizumi et al. | 128/653 |
| 5,207,227 | 5/1993 | Powers | 128/691 |
| 5,233,994 | 8/1993 | Shmulewitz | 600/454 |
| 5,445,157 | 8/1995 | Adachi et al. | 600/473 |
| 5,588,437 | 12/1996 | Byrne et al. | 128/691 |

OTHER PUBLICATIONS

Cancer Letters 84 (1994) Michael Anbar—Hyperthermia of the cancerous breast: analysis of mechanism; pp. 23–29.
Journal of Pain and Sympton Management; Special Article—Role of Nitric Oxide in the Physiopathology of Pain; Michael Anbar and Barton M. Gratt; pp. 225–254.
Fast Dynamic Area Telethermometry (DAT) of the Human Forearm With A Ga/As Quantum Well Infrared Focal Plane Array Camera; Michael Anbar, M. W. Grenn, M.T. Marino, L. Milescu and K. Zamani; pp. 105–118.
Manifestiation of Neurological Abnormalities Through Frequency of Skin Temperature Regulation; Michael Anbar, James C. Montoro, Kyu Ha Lee and Sean D'Arcy; 1991; pp. 234–241.
Biomedical Thermology; 13; Local; "Micro" Variance In Temperature Distribution Evaluated By Digital Thermography;Michael Anbar and Robert F. Haverley; pp. 173–187, 1994.
Simultaneous Acquisition of Thermal and Visible Images in A Scanning Infrared Camera; Shahram Hejazi, Omid A. Moghadam, Robert A. Spangler and Michael Anbar; SPIE vol. 2020 Infrard Technology XIX, pp. 510–516.

*Primary Examiner*—Brian L. Casler
*Attorney, Agent, or Firm*—Hodgson, Russ, Andrews, Woods & Goodyear LLP

[57] ABSTRACT

The present invention comprises methods for cancer detection involving the measurement of temporal periodic changes in blood perfusion, associated with immune response, occurring in neoplastic lesions and their surrounding tissues. Particularly, the method for cancer detection involves the detection of non-neuronal thermoregulation of blood perfusion, periodic changes in the spatial homogeneity of skin temperature, aberrant oscillations of spatial homogeneity of skin temperature and aberrant thermoregulatory frequencies associated with periodic changes in the spatial homogeneity of skin temperature.

10 Claims, 2 Drawing Sheets

DETECTION OF CANCEROUS LESIONS BY THEIR EFFECT ON THE SPATIAL HOMOGENEITY OF SKIN TEMPERATURE

CROSS-REFERENCE TO RELATED APPLICATION

The present application is a continuation-in-part of application Ser. No. 08/368,161, filed Jan. 3, 1995 now U.S. Pat. No. 5,810,010.

BACKGROUND OF THE INVENTION

1. Field of Invention

The present invention relates generally to cancer detection involving the measurement of temporal periodic perfusion changes associated with immune response in tissue surrounding cancerous lesions. While this has applications to cancer detection throughout the human body, it is particularly applicable to a breast cancer screening test involving the measurement of temporal changes in perfusion over large areas of the breasts to identify cancer. Generally, a full work-up, such as ultrasonic scan, needle or incision biopsy, or stereotactic biopsy based on detailed mammographic image, is preceded by a positive finding on a breast cancer screening test. The present invention has many significant differences and advantages over breast cancer screening tests known in the art, as well as general cancer detection methods.

2. Prior Art

Cancerous lesions have been generally located by their space occupying properties detectable by palpation or by imaging techniques, such as X-ray radiography, X-ray computerized tomography (CT), ultrasonic imaging, or magnetic resonance imaging (MRI). In certain cases, such as breast cancer, detection of cancer is made possible by the enhanced blood supply (hyperperfusion) associated with the neoplastic lesion. In shallow lesions, such as breast cancer, this hyperperfusion results in local hyperthermia.

Hyperthermia of cancerous breasts has been used to detect breast cancer. In classical thermal imaging (thermography) the skin temperatures of both breasts is measured either by liquid crystal contact thermography (LCCT) or by infrared imaging. The bulk temperatures of both breasts is also measured by microwave telethermometry. The difference between the temperatures of the cancerous breast and the non-cancerous breast is often not identified as a signal for further cancer testing since the temperature difference is very similar to differences between two non-cancerous breasts. Temperature differences may occur for a number of reasons unrelated to the presence of cancer. Therefore, the sensitivity and specificity of breast cancer detection by such measurements of temperature are too low to make them useful as a practical screening test. The present invention does not use differences between the temperatures of the two breasts as a diagnostic criterion.

X-ray mammography (XRM) is a widely used technique for breast cancer screening prior to full diagnostic work-ups. It uses the higher density of calcium minerals and the higher absorbance of X-rays in calcium atoms, due to the photoelectric effect, to detect microcrystals of calcium minerals, generally calcium phosphates, that deposit interstitially in cancerous tissue. The characteristic shadow of the relatively opaque microcrystals of calcium minerals on the radiograms indicates their presence in tissue. A draw-back of XRM as a breast cancer screening test is the occurrence of microcalcification or calcification in benign lesions, hence only a fraction of breasts that manifest microcalcification contain malignant tissue. False positive XRM results are common, and lead to full diagnostic work-ups which often prove to be negative for breast cancer. The present invention does not use calcification or microcalcification of tissue as a diagnostic criterion.

Since pathological microcalcification occurs subsequent to tumor formation, it occurs later than the proliferation of cancerous cells, which produce nitric oxide, and the immune response to neoplastic cells, which invokes macrophage activity that also produces nitric oxide. Therefore, breast cancer detection by XRM occurs later than detection by the present invention.

Furthermore, the present invention is significantly less expensive than XRM. The equipment needed for the present invention costs less than one third the cost of XRM equipment. The facility required for the present invention is substantially less expensive (radiation shielding is required with XRM), the personnel needed for the present invention procedure requires substantially less training and is not exposed to any professional hazard (ionizing radiation). Moreover, the present invention does not require an expert's image recognition, whereas XRM requires the expertise of a radiologist. Consequently, the actual cost of the present invention is significantly lower than the cost of XRM. A benefit/cost analysis shows that even if the sensitivity and specificity of the present invention test simply match those of XRM, the present invention is more beneficial, even on purely economic grounds.

Additionally, the present invention poses zero risk to the patient. On the contrary, even with the use of modern mammographic equipment there is a finite risk of cancer induction by XRM. The risk is at least 1 in 1,000,000 tests, and more likely substantially larger. Also, the present invention causes much less discomfort to the patient than the squeezing of the breasts that must be done in adequate mammography.

The current sensitivity and specificity of XRM are far from satisfactory, especially in flat and in dense breasts. The present invention is substantially more sensitive and specific than classical thermal imaging, (which was shown to be only slightly less effective than XRM) and, therefore, is superior to XRM in diagnostic efficiency.

Unlike XRM which is dependent uon microcalcification to make the tumor detectable, the present invention directly detects cancerous calls and the immune response to them and, therefore, detecfts breast cancer substantially earlier than XRM. Since the outcome of treatment of breast cancer is more favorable the earlier cancer is detected, the present invention has a substantial advantage over XRM in improving public heath.

I. Dynamic Area Telethermometry

Dynamic Area Telethermometry (DAT) is a known concept and described fully in the 1991 publication of Dr. Michael Anbar, *Thermology* 3 (4) :234–241, 1991. there is, however, no known practical application for DAT in the public domain. It is a non-invasive, functional test of the autonomic nervous system, that monitors changes in the spectral structure and spatial distribution of thermoregulatory frequencies (TRF's) over different areas of the human skin. Grounded in the science of blackbody infrared radiation as measured by infrared imaging, DAT derives information on the dynamics of heat generation, transport, and dissipation from changes in the temperature distribution over areas of interest. Changes can be detected in the average temperatures of area segments or in the variances of those averages; the variances measure the homogeneity of the temperature distribution and, therefore, the homogeneity of cutaneous perfusion. As shown by Dr. Anbar in the European J Thermology 7:105–118, 1997, under conditions of hyperperfusion the homogeneity reaches a maximum and the amplitude of its temporal modulation is at a minimum. From the periodic changes in temperature distribution over different skin areas, the thermoregulatory frequencies of the processes that control the temperature in the given areas can be derived.

From the periodic changes in the spatial homogeneity of skin temperature (HST), the processes that control the saturation of the cutaneous capillary bed can be derived. HST is the reciprocal of the spatial coefficient of variation of temperature in small ("micro") areas of skin (<100 mm$^2$): HST=average temperature divided by the standard deviation of the average temperature (HST is a dimensionless parameter). HST is determined by the structure of cutaneous vasculature and by its heat dissipatory activity. As perfusion is enhanced, more capillaries are recruited as blood conduits and HST increases. Unlike average temperature, HST is affected mainly by the behavior of the cutaneous capillaries and to a much lesser extent by the blood flow in subcutaneous vessels. The neuronal control of HST is, therefore, different from that of skin temperature. Consequently, HST is an independent physiological hemodynamic parameter. Like the average temperature of unit areas of skin, HST oscillates as a function of the temporal behavior of perfusion. Since the rate of increase of HST with the extent of perfusion is much higher than that of temperature, the extent of its change and the amplitude of its modulation are significantly higher than those of temperature change and temperature modulation. A static image of HST is, therefore, more informative than a classical thermogram. The concept of HST has been fully described by Dr. Michael Anbar in Biomedical Thermology, 13:173–187, 1994.

Quantitative DAT requires high-precision measurement of infrared flux (corresponding to <0.01° C.), low electronic and instrumental noise (<0.0005° C. equivalent of electronic or thermal noise), and long-term stability (drift of <0.1° C./hr). All these are attainable with current commercial equipment. The minimal resolution required for DAT is an image field of 128×128 pixels, which can be optically zoomed to cover an area of 10 to 10000 cm$^2$ (0.06 mm$^2$ to 0.6 cm$^2$/pixel). Current technology provides for an improved image field of 640×480 pixels. To guarantee correct recognition and precise location of the anatomic features studied, it is beneficial to simultaneously generate a reflective image of exactly the same body area (to precisely record the anatomic features), and superimpose the reflective image over the emissive image to assure precise registration of any thermal abnormalities found. This concept has been fully described in a publication of Dr. Michael Anbar, *SPIE Proceedings* 2020:510–517, 1993.

DAT is useful in the diagnosis and management of a large variety of disorders that affect neurological or vascular function. DAT is used to measure the periodicity of changes in blood perfusion over large regions of skin so as to identify a locally impaired neuronal control, thereby providing a quick and inexpensive screening test for skin cancer and for relatively shallow neoplastic lesions, such as breast cancer. The different clinical applications of DAT are fully described by Dr. Michael Anbar in 1994 in a monograph entitled "Quantitative and Dynamic Telethermometry in Medical Diagnosis and Management", CRC Press Inc. September, 1994.

The substantially lower cost of infrared equipment and the substantially lower personal training requirements make DAT tests substantially less costly than radiological, ultrasonic, or Nuclear Magnetic Resonance (NMR) based computerized imaging tests, such as CT (computerized tomography), SPECT (single photon emission computerized tomography), PET (positron emission tomography), or MRI (magnetic resonance imaging). Being utterly non-invasive, DAT tests are risk free and cause significantly less discomfort to the patient than some of the neuromotor tests, such as EMG, or nerve conduction tests. They also take significantly less time than other scanning tests (CT, MRI, or ultrasonic tests, respectively).

II. Measurements

A. Thermoregulation

Skin, the largest organ of the human body, plays a major role in regulating the body's core temperature. In its heat dissipatory role, skin generally becomes warm when the body needs to dissipate excessive heat, and turns cold when the body must preserve heat. Under moderate environmental conditions, skin temperature depends primarily upon the blood flow in the vasculature below the skin surface. Thus, in a similar manner as other neurological or neuromuscular tests, substantial diagnostic information is embedded in the dynamic behavior of the thermoregulatory system.

Skin temperature reflects the physiological behavior of cutaneous blood flow which is modulated by the neurological control of pertinent arteries and arterioles. Observing skin temperature at any point on the skin as a function of time can provide direct information on the neurological control of the vasculature. Neurological disorders can, therefore, be associated with abnormal temporal behavior of skin temperature, in addition to changes in spatial distribution of thermoregulatory function, both of which lend themselves to quantitative assessment.

Although skin temperature may vary over a wide range, depending upon the environment and on the level of metabolic activity, it is regulated under normal conditions. This regulation may be occasionally less stringent, like during sleep but even then, some skin regulation is retained. Like any regulated parameter, including core temperature, skin temperature is expected to oscillate around a set point, even if the value of the set point does not remain constant. Even a simple thermostated system, such as a forced air heated and cooled house, will show temperature oscillations stemming from temperature over-shooting and delays due to imperfect thermostats and different rates of response and relaxation of the individual heating and cooling processes. In the human body, skin temperature maintenance is due, in substantial part to neuronal thermoregulation of vasoconstriction and vasodilation of the vasculature, thereby causing a characteristic modulation of blood perfusion, unless the neuronal thermoregulation is inhibited or taken over by a non-neuronal thermoregulatory control, such as nitric oxide (NO). In a complex regulated system, such as the human body, where there are several levels of non-linear regulatory processes interacting with each other, many thermal regulatory oscillations are superimposed on each other. To deconvolute these into systemic, regional, and local thermal regulatory processes, one has to probe different parts of the body, and different regions of organs.

In order to maintain or change skin temperature, the neuronal thermoregulatory system constricts or dilates its blood vessels to change the rate of blood flow in the vessels. As indicated above, this is not the case if the neuronal thermoregulation is inhibited in certain regions by an independently functioning agent, such as NO. That region is then under non-neuronal thermoregulatory control.

NO has been recognized as a ubiquitous vasodilatory chemical messenger. Its main role appears to be synchronization of intercellular and inter organ functions, as it diffuses freely in the interstitial space. This has been discussed extensively by Dr. Anbar in J. Pain Sympton Manage 14:225–254, 1997. It can, therefore, inhibit sympathetic vasoconstrictive control in substantial regions of the microvasculature and cause regional hyperperfusion. Subcutaneous and cutaneous hyperperfusion are manifested as hyperthermia of the overlying skin. Augmented immune response, such as encountered in local infections, autoimmune diseases, and cancer, is associated with enhanced NO production. Under certain conditions, such as in breast cancer, autocatalytic production of NO may occur, which results in oscillatory vasodilation, independent of and substantially different from the temperature oscillations of perfusion caused by the neuronal thermoregulatory system.

B. Mechanism of Local Hyperthermia of Cancerous Breasts

Cancer associated breast hyperthermia is caused by impaired neuronal thermoregulation. This impaired neuronal control is caused by excessive production of NO by breast cancer cells and by macrophages that react to the neoplastic tissue. This activity is an expression of the immune response, because NO generated by macrophages is a major factor in killing of microorganisms or of mammalian cells recognized as alien. This mechanism is described fully in a 1994 publication of Dr. Michael Anbar, *Cancer Letters* 84(1):23–29, 1994. The generation of NO by cancer cells increases their blood supply and enhances the probability of metastasis. The breast cancer cell and macrophage generated NO, which diffuses freely throughout the surrounding tissues, interacts with the vasoconstrictive receptors in the arterioles so as to vasodilate the vasculature. This results in enhanced perfusion of the capillary bed. As a consequence of the characteristic multiphasic synergistic action of NO, this augmented perfusion enhances the growth of breast cancer cells. The rate of production of NO is further enhanced by the presence of ferritin, the level of which is significantly elevated in breast cancerous tissue. $Fe^{2+}$ released from ferritin is used to produce more NO synthase (NOS), an iron carrying enzyme which produces NO from arginine, and thus results in a further increase in the rate of production of NO.

Furthermore, NO has been shown to release $Fe^{2+}$ from ferritin, by forming an NO-ferritin complex. This results in an autocatalytic production of NO. $Fe^{2+}$ reacts with nitrite, the oxidation product of NO, to reform NO, and it also eliminates superoxide radicals ($HO_2$) which are normally the major scavengers of NO. This maintains the local high level of NO, and the hypoperfusion of the capillary bed. The ferritin dependent enhancement of NO production seems to be specific to neoplastic cells and is less likely to occur in other inflammatory situations, including those induced by microorganisms.

NO diffuses readily interstitially; therefore, the volume of the capillary bed that is hyperperfused is many-fold larger than that of the tumor and its immediate surroundings. This explains the extensive regional hyperthermia associated with minuscule antigenic tumors. The rate of NO production in the cancerous breast is also amplified by the positive effect of the local temperature on NO production by the cancerous cell and by macrophages. All those autocatalytic effects overshadow the negative feedback of NO level on the rate of enzymatic NO production.

Like any autocatalytic process, the rate of NO production is expected to oscillate. The rate of NO production is expected to rise exponentially due to the positive feedback of $Fe^{2+}$ and of temperature, and then fall when certain precursors, such as, arginine or oxygen, are temporarily locally depleted. A similar positive feedback, resulting in vascular oscillations, has been demonstrated for NO under ischemic conditions in the brain, where the lack of oxygen results in lower production of NO and a subsequent vasoconstriction, which further limits oxygen supply.

NO generated by the cancerous cells and by macrophages perfuse throughout the capillary bed and inhibit, or even take complete control of the modulation of blood perfusion from the neuronal system and, therefore, overshadow the neuronal thermoregulatory temperature oscillations. Since the extent of perfusion and the surface temperature of the overlying skin follow the same oscillatory behavior, the temporal behavior of skin temperature over the cancer cell region does not follow the normal neuronal thermoregulatory modulation in blood perfusion. The region, therefore, does not maintain normal temperature oscillations or thermoregulatory frequencies resulting therefrom.

The frequencies of temperature oscillations observed over the cancerous breast differ substantially from those observed over the non-cancerous (normal) breast. The oscillations over a normal breast are caused by the neuronal thermoregulatory processes, which follow several characteristic bands of frequencies. The cancerous area of the breast, on the other hand, which loses its neuronal thermoregulatory control due to the over-production of NO, is characterized by the disappearance of the neuronal oscillations and the appearance of oscillations due to the autocatalysis of NO production, with their typical frequency bands. Since the latter autocatalytic processes, which are controlled by the temporary local depletion of one of the precursors of NO, are utterly different in nature from the neurological feedback processes manifested in the neuronal frequency bands, there is no possibility of frequency overlap of these entirely different processes over all frequency bands. The disappearance of the neuronal frequencies over substantial parts of the cancerous breast is sufficient to identify pathology. Furthermore, the appearance of the autocatalytic frequencies characteristic of NO over-production is, by itself, sufficient to identify pathology. The substitution of one set of frequency bands by the other is an even more strict criterion of pathology.

Under conditions of extravascular NO overproduction and its consequent hyperperfusion, HST reaches a maximum value that oscillates at a frequency that depends on the modulated autocatalytic rate of NO production. The frequency bands of the modulation of HST can be used, therefore, as independent criteria of pathology. The combination of the temperature and HST criteria increase the sensitivity and specificity of the DAT test.

Since, unlike classical thermography of the breast, the DAT test does not use the absolute temperature or temperature differences as a diagnostic parameter, there is less need to allow the patients to reach thermal equilibrium with the environment. This means faster turnover of patients, hence lower cost per test. Moreover, the environment does not have to be strictly controlled, as long as it does not contain modulated infrared emissions in the frequency ranges of interest, that might be reflected from the skin. This lowers the cost of the installation. Since the overwhelming majority of screened subjects are free of malignancy, the administration of the test can be fully computerized and does not require medical expertise. The extensive computerization which allows the use of easily trained semi-skilled personnel, provides a substantially lower cost of this screening test, as compared with the prior art (including the classical thermological tests).

C. Alternative Methods to Measure Periodic Changes in Perfusion

As stated, DAT is the method of choice to measure modulation in blood perfusion. Microwave thermometry of the bulk tissue and thermometry of the skin using arrays of thermistors, are two alternative methods to dynamically measure temperature. Microwave thermometry has, however, a significantly lower spatial resolution (by a factor of 10,000) and lower sensitivity (by a factor of 10 to 100), and it may require direct contact of the electrodes (antennas) with the breast, which calls for skill and additional time. Area thermometry by thermistors with adequate spatial resolution requires the mounting of many hundreds or even thousands of thermistors all over the breasts, which is a prohibitively cumbersome process. Liquid crystal contact thermography (LCCT) provides inadequate low precision (>0.5° C.) and too long response times to be useful in quantitative dynamic measurements.

Other methods of continuously measuring the modulation of perfusion of the capillary bed in the breast include ultrasound (measuring changes in ultrasonic impedance, because the speed of sound is temperature dependent and because of changes in the average density of hyperperfused tissue), or by measuring changes in the average velocity of erythrocytes by Doppler shift. However, ultrasonic measurement of perfusion cannot be done simultaneously on all areas of one or both breasts. It also requires a highly skilled technician to measure the changes in perfusion in different areas. Further, it is necessary to apply a coupling lotion in order to make contact with the ultrasonic probe and the breast. The application of such coupling lotion and the contact of the ultrasonic probe may alter the perfusion by affecting the thermal and tactile neuronal sensors.

Another method of measuring modulation in blood perfusion is infrared Doppler velocimetry (IRDV), which measures the Doppler shift of the near infrared radiation (about 1 $\mu$m) reflected from erythrocytes. IRDV, however, cannot monitor modulation of blood perfusion over large areas in a reasonable time (it would take hours to accumulate the same information on the temporal behavior of blood perfusion that can be measured in about 30 seconds by DAT).

Another method for measuring modulation in blood perfusion is single photon emission computerized tomography (SPECT), which measures the local concentration of radioactively labeled compounds in tissues inside the human body. Red blood cells can be labeled by a radioactive isotope and their concentration in a tissue of interest is a measure of perfusion. SPECT, however, does not measure concentrations with a precision that provides for monitoring small, i.e., about 1%, modulations of perfusion. Moreover, SPECT entails radiobiological risk to the patient, is more cumbersome and time consuming, and involves much more expensive instrumentation compared with DAT.

Another method of measuring modulation in blood perfusion is impedance plethysmography (because the ionic conductivity depends on the amount of plasma between the electrodes). This method, which requires the mounting of an array of electrodes on the two breasts by a skilled technician before any measurement can be done (which makes it substantially more expensive), is also less sensitive to minute oscillations; further, its spatial resolution (limited by the number of electrodes used) is significantly lower than achieved by DAT.

Yet another method of continuously measuring the modulation in perfusion of the capillary bed in the breast is MRI. MRI can be used to dynamically monitor blood perfusion and detect characteristic oscillations associated with the autocatalytic NO controlled mechanism. However, MRI requires much more expensive instrumentation than DAT (by a factor of 30 to 60), and an examination would be much more cumbersome and time consuming. MRI, more importantly, can be used to identify deeply situated cancerous lesions, ones that do not affect cutaneous or subcutaneous perfusion, and are, therefore, not amenable to DAT tests.

Since the modulation of blood perfusion of the cancerous breast is directly related to the modulation of NO in the affected tissue, measuring the concentration of NO and its modulation could be used as an alternative diagnostic method for cancer detection. The most preferred method of measuring the concentration of NO in human tissues is by electron paramagnetic resonance (EPR) operating in an imaging mode. Imaging EPR is conceptually very similar to MRI, however, it uses different electromagnetic frequencies. The cost of an EPR imaging test will, therefore, be comparable with an MRI test. Like MRI, EPR imaging can also be used to identify deeply situated cancerous lesions that do not affect cutaneous or subcutaneous perfusion and are, therefore, not amenable to DAT tests.

BRIEF DESCRIPTION OF THE DRAWINGS

The invention will become more readily apparent from the following description of preferred embodiments thereof shown in the accompanying drawings, wherein.

DETAILED DESCRIPTION OF THE PREFERRED EMBODIMENTS

Figure 1:
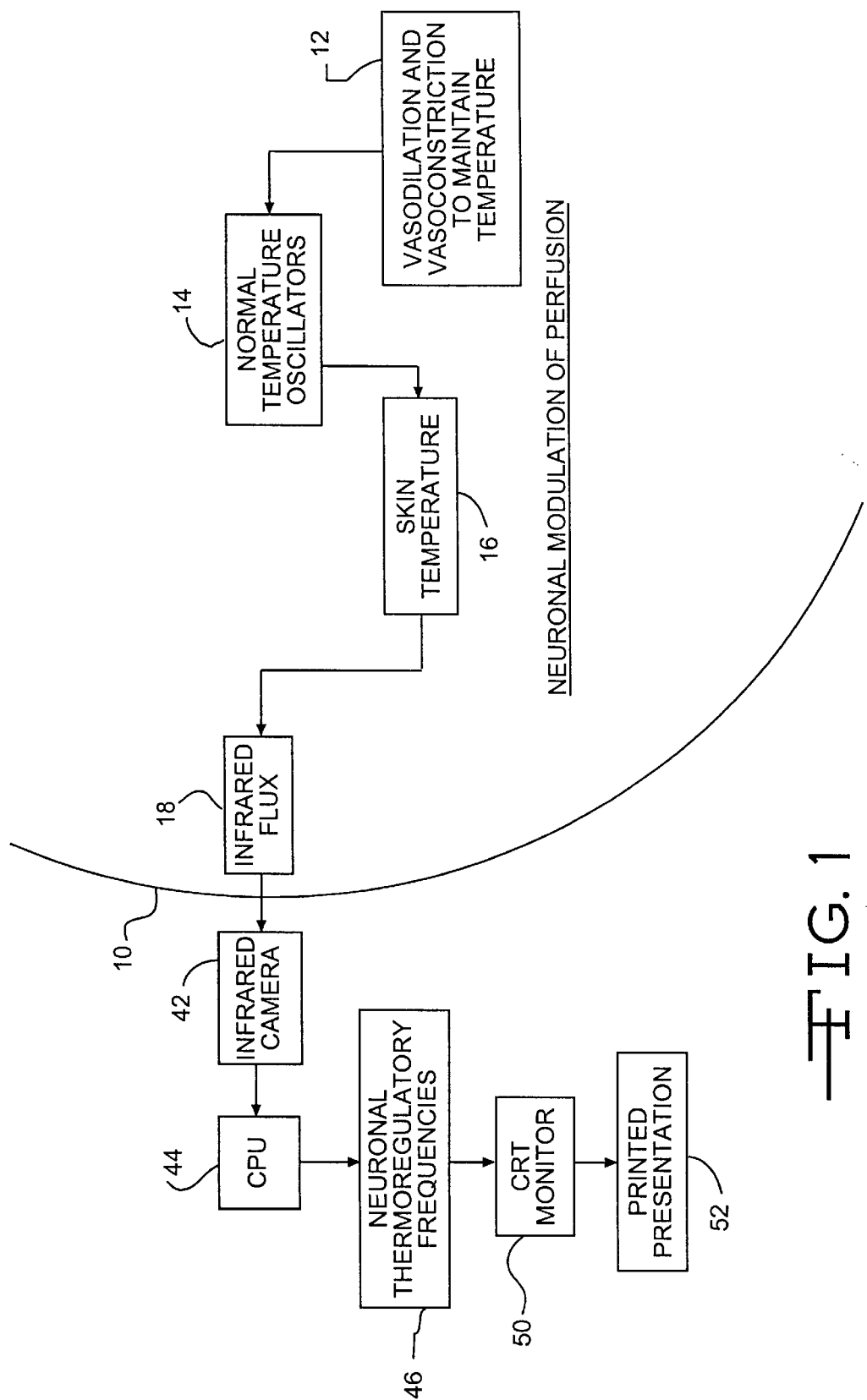
FIG. 1 is a schematic representation of the neuronal modulation of perfusion in a healthy breast.
Figure 2:
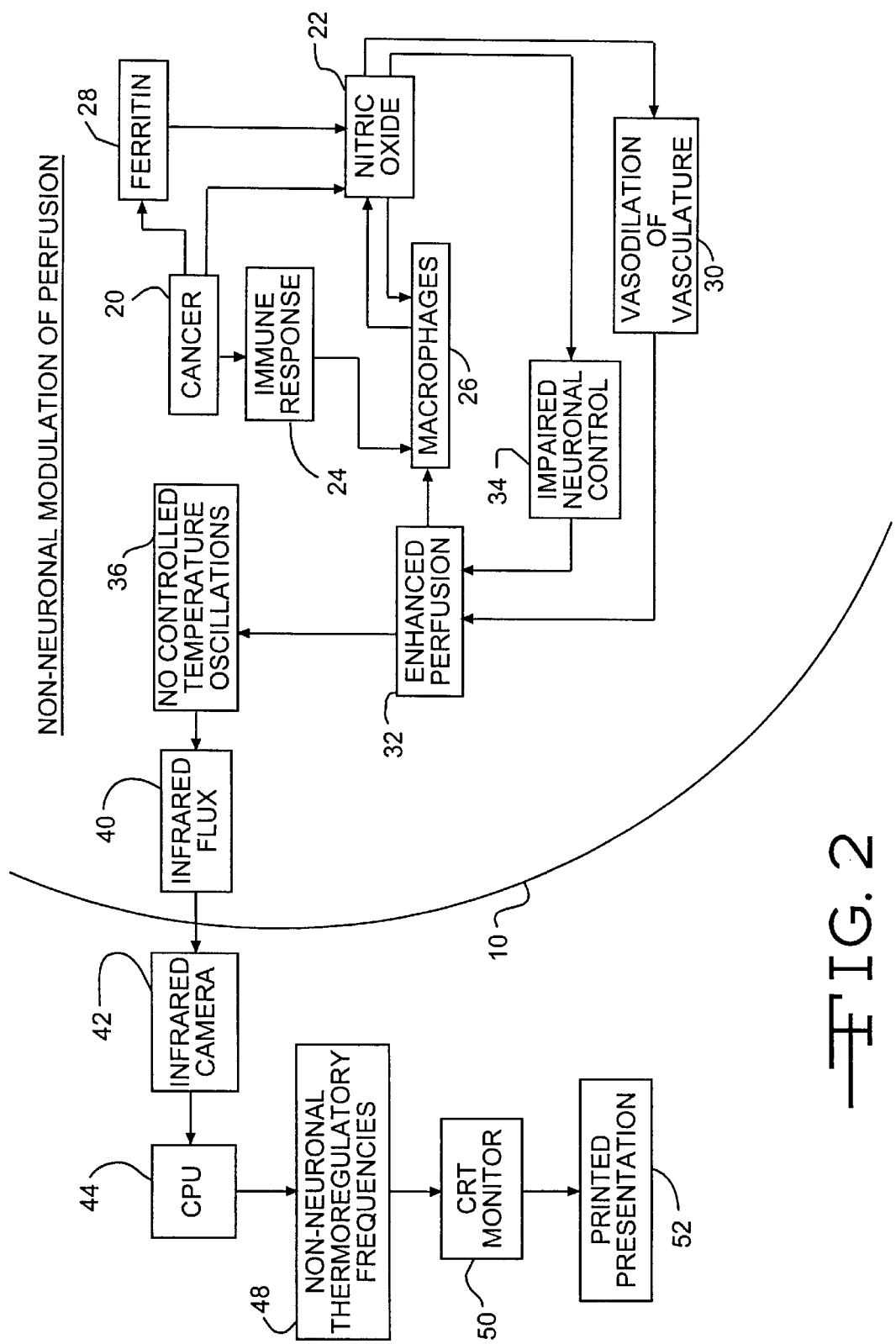
FIG. 2 was a schematic representation of the modulation of perfusion in a cancerous breast and showing each of the steps of detection of cancerous lesions according to the present invention.

As shown in FIG. 1, a non-cancerous region of the breast 10 maintains a required temperature by neuronal modulation of blood perfusion 12. Furthermore, this modulation of blood perfusion generates temperature oscillations 14 from which a infrared flux 18 is detectable corresponding skin temperature 16. As shown in FIG. 2, a cancerous 20 region of the breast 10 contains cells that produce NO 22 and it also provokes an immune response 24 which enhances the activity of macrophages 26 that also produce NO 22. This NO production is enhanced by the elevated level of ferritin 28 in the breast cancerous tissue. Moreover, the presence of NO vasodilates the vasculature 30 causing enhanced perfusion of the capillary bed 32. The presence of NO also impairs neuronal control 34 of vasoconstriction and vasodilation of the vasculature thereby changing the modulation of perfusion of the capillary bed 32 and the temperature oscillations 36 manifested therefrom. Aberrant modulation of perfusion provides an aberrant infrared flux 40.

According to the present invention, an infrared camera 42 is positioned to provide infrared images of the human body, for example breast 10. A preferred camera is equipped with a 640×480 focal plane array (FPA) GaAs quantum-well infrared photodetector (QWIP). Such a camera can record modulation of skin temperature and its homogeneity with a precision greater than ±2 millidegrees C, i.e., less than 1/20 of physiological modulation of temperature and of homogeneity of human skin. The infrared images are transmitted to a CPU 44 which processes the recorded infrared flux information to determine whether the breast is normal or cancerous. In the former case, modulation of perfusion changes of the spatial homogeneity of the skin temperature are dictated by neuronal thermoregulatory frequencies 46 (FIG. 1). In a cancerous breast, the spatial homogeneity of skin temperature is dictated by non-neuronal thermoregulatory frequencies 48 (FIG. 2). This data is output on a CRT monitor 50. The CPU outputs printed presentations 52 of the collected infrared data in a useable ready format, as will be explained in detail presently.

Thus, the screening technique of the present invention uses the characteristic changes in the temporal behavior of blood perfusion caused by enhanced NO production by cancerous cells 20 and macrophages 26 and amplified by ferritin 28 to detect an immune response 24 induced by neoplastic disease. The temperature oscillation of blood perfusion associated with the autocatalytic production of NO, as well as the diminution or disappearance of the neuronal TRFs are used as the diagnostic parameters. Like skin temperature, HST changes from neuronal to NO controlled modulation. The TRFs of HST are, therefore, additional independent diagnostic parameters.

The neuronal and autocatalytic oscillations are measured by fast Fourier transform (FFT) analysis, an analysis method well known in the art, of the temporal behavior of breast perfusion (manifested in the temporal behavior of breast temperature and of HST). As discussed above, modulation of perfusion of the capillary bed in the breast can be continuously measured by several techniques. Because of its sensitivity, fast response time, speed of data acquisition and low cost, DAT is the preferred method of measuring modulation of perfusion of the capillary bed and identifying aberrations in parts of human tissue. It possesses a sensitivity of up to 0.001° C. (i.e., about 50 times smaller than the level of temperature modulation under conditions of normal perfusion; the autocatalytic process is expected to have an even higher level of modulation) and a response time of <10 msec. The TRFs of HST are derived from the same DAT data, using the same computational technique, only that in this case the measured parameter used in the calculation is the spatial "micro" variance of temperature.

As thoroughly described in U.S. application Ser. No. 08/368,161, which is licensed to the assignee of the present invention and incorporated herein by reference, DAT facilitates the simultaneous monitoring of the complete areas of both breasts including their lateral views by using mirrors. Such simultaneous monitoring over time of complete areas of both breasts is the preferred method. It allows for the accumulation of hundreds of sequential thermal images that are then subjected to FFT to extract the frequencies and amplitudes of periodic changes at each pixel of the image. To measure the HST, the image is subdivided into a matrix of small areas, each corresponding to 64 mm$^2$ of skin, and the temperature values of the pixels in each subarea of the image are averaged. The variance of the average temperature is used to calculate the HST of each subarea. The HST values of all the accumulated images are then analyzed by FFT to extract the corresponding frequencies of the standard deviation of average temperature requires a highly stable, high resolution, highly sensitive, computerized infrared camera, preferably operating in the 8 to 14 $\mu$m range. To meet the specific DAT needs it is preferred that the camera's computer be programmed to quantitatively analyze the temporal behavior of many thermal images with a sufficient resolution, e.g., 640×480 pixels. Using a state of the art 640×480 camera, the geometry of a 300×600 pixel image of both breasts can be analyzed. While successful results can be achieved by analyzing the temporal behavior of at least 128 thermal images, it is most preferred to measure 1024 thermal images. These images can be temporarily stored to perform the FFT on the time series of temperature values of each pixel or subarea. The FFT yields the frequency spectra of each pixel together with the relative amplitude of each TRF. The software then tabulates or displays the spatial distribution of the TRFs within a given range of relative amplitudes over the image. The same procedure is followed with the HST data.

When TRFs are displayed with amplitudes above a given threshold (e.g., above 5% of the total thermal modulation, or a certain cut-off value in the rank order of amplitudes) a subset of characteristic neuronal frequencies over areas of breasts free from cancer-enhanced immune response is identified; these TRFs are significantly attenuated or completely absent in areas overlying breasts with neoplastic lesions. The latter areas are characterized by substantially different TRFs caused by the autocatalytic production of NO and exhibit, therefore, the non-neuronal thermoregulatory behavior. Also the latter areas are, therefore, characterized by aberrant modulation of blood perfusion and aberrant temperature oscillations. A hard copy image is then generated to allow an expert to anatomically identify the location of the aberrant area, or areas. The infrared camera can be equipped also with video CCD to produce a reflective (visual) image of the patient's breasts. The reflective image allows precise anatomical location of areas with aberrant temporal behavior, information needed for further work up of such a patient.

The computer algorithms that facilitate this computation are as follows:

A. Use of temperature values of individual pixels and the computation of TRFS.

1. The computerized camera takes an image of the infrared flux (300×600 pixels) and converts it into a thermal image where each pixel has a certain temperature value. This process is repeated, preferably, thirty times a second until 1024 thermal images have been accumulated and stored.

2. The areas of interest on the image are subdivided into subareas of 36 to 64 pixels, each corresponding to one to four square millimeters of skin, depending on the resolution of the camera. The average temperature and the standard deviation of each of the subareas in each of the 1024 images are then calculated. These average temperature values constitute a single time series that is then subjected to FFT analysis to extract the contributing frequencies and their relative amplitudes. The computer stores the FFT spectrum for the given group of pixels. The computer repeats the same procedure for each of the selected groups of pixels of the image.

3. The computer picks the FFT spectra of the selected spots and displays colored bitmaps of the relative amplitudes in any exhibited range of frequencies to thereby identify clusters of spots with abnormal frequencies.

4. If procedure #3 does not identify definitely aberrant clusters, the computer prints out a message that the findings are negative and the patient is normal. Otherwise, the computer proceeds with procedure #5.

5. The computer examines all the pixels in the aberrant areas identified in procedure #3 for the 10 most prominent frequencies to identify frequencies that are characteristic of cancer.

6. If procedure #3 identifies a definitely aberrant area, while procedure #5 turns out negative, the computer prints out a color image of the breasts. If procedure #5 yield a confirmation, the computer prints out another color image with the aberrant areas.

B. Use of HST values and the computation of HST TRFs.

1. The computer subdivides the image into 2048 square subareas of 64 pixels each (corresponding to approximately 64 mm$^2$ of skin), and calculates the average temperature (AVT) value and standard deviation (SD) of each subarea. The SD values can be treated identically to the AVT values of groups of pixels according to procedures #A1 to A6.

2. The computer then calculates the HST value for each subarea: HST=AVT/SD. Time series of HST values are then analyzed by FFT to yield HST TRFs, following procedure #A2. Alternatively, time series of SD can be treated in the same fashion.

3. The next steps of the computation follow identical procedures to #A3 to A6, except that the absolute amplitude are in HST dimensionless units.

4. Following the last step of procedure #A6 with the HST TRFs finding, if positive, can be used to confirm the findings of the temperature TRFs. In this case, there are four independent diagnostic parameters and the printout of the findings must be done with a four color printer.

5. The printout of the visual image can be done in halftone monochrome on a transparent mat that can be overlaid on the aberrant area image, to precisely identify the anatomic position of the aberrant area.

The difference between normal and cancerous breasts is accentuated by a thermal challenge (cooling) of the breasts, which affects only the neuronal thermoregulatory system and therefore affects only TRFs in areas that are not vasodilated by excessive extravascular NO production. The computer is programmed to look for the frequency bands of the neuronal and the NO controlled TRFs in every statistical square subset of pixels (e.g., 36 or 64 pixels) of the FFT processed image. If the computer does not find any statistical subsets with neuronal TRFs having exceptionally low or nil amplitude (except in the periphery of the image which does not depict skin), and no pixels or subareas are found to have the NO controlled autocatalytic TRFs with a significant amplitude, the findings of the test are declared as negative (i.e., normal). This finding is then confirmed by computing and analyzing the HST TRFs. If the computer finds certain pixels with exceptionally low neuronal TRFs and if those pixels exhibit the NO controlled autocatalytic TRFs, the test findings, preferably DAT test findings, will be classified as pathological. This finding is then confirmed by analyzing the HST data, as described for the uncooled breast. Cooling of the breasts (by a mild flow of forced air) attains maximal sensitivity and specificity. Such additional testing are administered as a confirmatory test only to patients who show a positive result on the uncooled test.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A method for detecting breast canter tissue in a human, comprising the steps of:

a) providing a detection device for detecting periodic changes in spatial homogeneity of temperature in areas of a human breast; and b) measuring, with the detection device, periodic changes in spatial homogeneity of temperature in areas of the human breast to thereby determine a likelihood of cancerous tissue in the human.

2. The method of claim 1 wherein the periodic changes in spatial homogeneity of temperature in areas of the human breast are measured using DAT.

3. The method of claim 1 wherein the detection device includes an infrared imaging and sensing system.

4. A method for detecting cancerous tissue in a human, comprising the steps of:

a) providing a device for measuring infrared flux emitted from a plurality of areas human skin;

b) measuring infrared flux emitted from the plurality of areas of the human skin;

c) detecting periodic oscillations in the infrared flux emitted from the plurality of areas of human skin; and d) detecting changes in the periodic oscillations in the infrared flux emitted from the plurality of areas of the human skin to thereby determine a likelihood of cancerous tissue in the human.

5. The method of claim 4 wherein the changes in periodic oscillation in the infrared flux emitted from the plurality of areas of the skin are detected using DAT.

6. The method of claim 4 wherein the measuring device includes an infrared imaging and sensing system.

7. A method for detecting cancer in a human body, comprising the steps of:

a) providing a detection device for detecting periodic changes in the spatial homogeneity of temperature in areas of human skin; and b) measuring with the detection device periodic changes in the spatial homogeneity of temperature in areas of the human skin to thereby determine a likelihood of cancer in the human body.

8. The method of claim 7 wherein the periodic changes in the spatial homogeneity of temperature in areas of the human skin are measured using DAT.

9. The method of claim 7 wherein the detecting device includes an infrared imaging and sensing system.

10. The method of claim 7 comprising the additional steps of:

a) providing a device for cooling the human skin; and b) cooling, with the cooling device, the human skin to accentuate the variances between cancerous and non-cancerous areas of the human skin.

* * * * *